US006589557B2

United States Patent
Straub et al.

(10) Patent No.: US 6,589,557 B2
(45) Date of Patent: *Jul. 8, 2003

(54) POROUS CELECOXIB MATRICES AND METHODS OF MANUFACTURE THEREOF

(75) Inventors: Julie Straub, Winchester, MA (US); Howard Bernstein, Cambridge, MA (US); Donald E. Chickering, III, Framingham, MA (US); Greg Randall, Somerville, MA (US)

(73) Assignee: Acusphere, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/881,289

(22) Filed: Jun. 14, 2001

(65) Prior Publication Data

US 2002/0019431 A1 Feb. 14, 2002

Related U.S. Application Data

(60) Provisional application No. 60/211,723, filed on Jun. 15, 2000.

(51) Int. Cl.[7] .............................. A61K 9/14; A61K 9/00
(52) U.S. Cl. ....................... 424/484; 424/489; 424/400; 424/405
(58) Field of Search ................. 424/484, 489, 424/9.52, 400, 405

(56) References Cited

U.S. PATENT DOCUMENTS

| 5,534,270 | A | | 7/1996 | De Castro |
|---|---|---|---|---|
| 5,585,112 | A | * | 12/1996 | Unger et al. ............ 264/4.1 |
| 5,587,143 | A | | 12/1996 | Wong |
| 5,853,698 | A | * | 12/1998 | Straub et al. ............ 424/9.52 |
| 6,046,191 | A | * | 4/2000 | Hamley et al. .......... 514/232.8 |
| 6,395,300 | B1 | * | 5/2002 | Straub et al. ............ 424/489 |
| 2002/0006951 | A1 | | 1/2002 | Hageman et al. |
| 2002/0028238 | A1 | | 3/2002 | Karim et al. |

FOREIGN PATENT DOCUMENTS

WO WO 9641626 A1 * 12/1996 .......... A61K/31/00

OTHER PUBLICATIONS

Ansel, et al., "Pharmaceutical Dosage Forms and Drug Delivery Systems," 6th Ed., (Williams & Wilkins 1995).
Bodmeier & Paeratakul, "Spherical Agglomerates of Water–Insoluble Drugs," *J. Pharma. Sci.* 78(11):964–67 (1989).
Genta, et al., "Improvement of dexamethasone dissolution rate from spray–dried chitosan microspheres," *S.T.P. Pharma Sciences* 5(3):202–07 (1995).
Imai, et al., "Rapidly absorbed solid oral formulations of ibuprofen using water–soluble gelatin," *J. Pharm. Pharmacol* 42:615–19 (1990).

* cited by examiner

Primary Examiner—Thurman K. Page
Assistant Examiner—Robert M. Joynes
(74) Attorney, Agent, or Firm—Holland & Knight LLP

(57) ABSTRACT

Celecoxib is provided in a porous matrix form wherein the dissolution rate of the drug is enhanced when the matrix is contacted with an aqueous medium. The porous matrix yields upon contact with an aqueous medium nanoparticles and microparticles of celecoxib having a mean diameter between about 0.01 and 5 $\mu$m and a total surface area greater than about 0.5 m$^2$/mL. The dry porous matrix preferably is in a dry powder form having a TAP density less than or equal to 1.0 g/mL. The porous celecoxib matrices preferably are made using a process that includes (i) dissolving celecoxib in a volatile solvent to form a drug solution, (ii) combining at least one pore forming agent with the drug solution to form an emulsion, suspension, or second solution, and (iii) removing the volatile solvent and pore forming agent from the emulsion, suspension, or second solution to yield the dry porous matrix of celecoxib. The resulting porous matrix has a faster rate of dissolution following administration to a patient, as compared to non-porous matrix forms of the drug.

25 Claims, 1 Drawing Sheet

POROUS CELECOXIB MATRICES AND METHODS OF MANUFACTURE THEREOF

This application claims priority to U.S. Ser. No. 60/211,723, filed Jun. 15, 2000.

BACKGROUND OF THE INVENTION

This invention generally relates to formulations of the drug celecoxib, and more particularly to methods of making formulations of such celecoxib to enhance its rate of dissolution.

The bioavailability of a drug, such as celecoxib, can be limited by poor dissolution of the drug into aqueous bodily fluids following administration. This rate-limiting step may therefore be critical to rapidly attaining therapeutically effective drug levels.

Traditional approaches to parenteral delivery of poorly soluble drugs include using large volumes of aqueous diluents, solubilizing agents, detergents, non-aqueous solvents, or non-physiological pH solutions. These formulations, however, can increase the systemic toxicity of the drug composition or damage body tissues at the site of administration.

Celecoxib, which is used for example in the treatment of inflammation of and inflammatory disorders, has some patient related drawbacks. These stem, in part, from its extremely low solubility in water, which makes it difficult to provide in suitable dosage form. There remains a need to develop improved formulations of the celecoxib which can be administered with improved oral bioavailability or, for example, as bolus injections.

Other approaches to delivery of poorly soluble drugs have focused on the physical form of the drug itself. Since the dissolution rate of a drug particle is directly related to its surface area available to contact the aqueous media at the site of administration or site of absorption, methods of preparing drugs in nanoparticulate form have been developed in an effort to maximize the drug surface area, as described, for example, in U.S. Pat. No. 5,534,270 to De Castro and U.S. Pat. No. 5,587,143 to Wong. Nanoparticles, however, can be difficult to produce and maintain in a stable form due to the tendency of the nanoparticles to flocculate or agglomerate, particularly without the presence of surface modifying agents adsorbed or coated onto the particles. Furthermore, milling or wet grinding techniques, which are typically employed for nanonization, can be undesirable, as it can take several days to process a single batch, scaling-up of the milling or grinding process can be difficult and/or costly, the process can be difficult to conduct aseptically, and it is difficult to eliminate shedding of milling media into the product.

Other efforts directed at enhancing the rate of dissolution have focused on delivering the drug as a dispersion in a water-soluble or biodegradable matrix, typically in the form of polymeric microparticles. For example, the dissolution rate of dexamethasone reportedly was improved by entrapping the drug in chitosan microspheres made by spray-drying (Genta, et al., *S.T.P. Pharma Sciences* 5(3):202–07 (1995)). Similarly, others have reported enhanced dissolution rates by mixing a poorly soluble drug powder with a water-soluble gelatin, which purportedly makes the surface of the drug hydrophilic (Imai, et al., *J. Pharm. Pharmacol.*, 42:615–19 (1990)).

Related efforts have been directed to forming relatively large, porous matrices of low solubility drugs. For example, Roland & Paeratakul, "Spherical Agglomerates of Water-Insoluble Drugs," *J. Pharma. Sci.*, 78(11):964–67 (1989) discloses preparing beads having a low solubility drug content up to 98%, wherein the beads have a porous internal structure. Such large beads, however, are unsuitable for parenteral administration, and the beads have less surface area and slower dissolution rates than smaller particles.

It is therefore an object of the present invention to provide compositions enhancing the dissolution rate of low aqueous solubility drugs, particularly celecoxib, and to provide methods of making such compositions.

It is another object of the present invention to provide celecoxib compositions in a formulation suitable for administration by a variety of routes, including, but not limited to, parenteral, mucosal, oral, and topical administration, for local, regional, or systemic effect.

It is another object of the present invention to provide compositions providing enhanced dissolution of celecoxib in a formulation suitable for administration by a variety of routes, including, but not limited to, parenteral, mucosal, oral, and topical administration, for local, regional, or systemic effect.

SUMMARY OF THE INVENTION

Celecoxib is provided in a porous matrix form wherein the dissolution rate of the drug is enhanced when the matrix is contacted with an aqueous medium. The porous matrix yields upon contact with an aqueous medium nanoparticles and microparticles of celecoxib having a mean diameter between about 0.01 and 5 μm and a total surface area greater than about 0.5 m$^2$/mL. The dry porous matrix preferably is in a dry powder form having a TAP density less than or equal to 1.0 g/mL.

The porous matrices that contain the celecoxib preferably are made using a process that includes (i) dissolving celecoxib in a volatile solvent to form a drug solution, (ii) combining at least one pore forming agent with the drug solution to form an emulsion, suspension, or second solution, and (iii) removing the volatile solvent and pore forming agent from the emulsion, suspension, or second solution to yield the dry porous matrix of celecoxib. The resulting porous matrix has a faster rate of dissolution following administration to a patient, as compared to non-porous matrix forms of the drug. The pore forming agent can be either a volatile liquid that is immiscible with the drug solvent or a volatile solid compound, preferably a volatile salt. If the pore forming agent is a liquid, the agent is emulsified with the drug solution. If the pore forming agent is a solid, the agent is (i) dissolved in the drug solution, (ii) dissolved in a solvent that is not miscible in the drug solvent and then emulsified with the drug solution, or (iii) suspended as solid particulates in the drug solution. Optionally, hydrophilic excipients, wetting agents, and/or tonicity agents may be added to the drug solvent, the pore forming agent solvent, or both. The solution, emulsion, or suspension of the pore forming agent in the drug solution is then processed to remove the drug solvent and the pore forming agent, as well as any pore forming agent solvent. In a preferred embodiment, spray drying, optionally followed by lyophilization, fluid bed drying, or vacuum drying, is used to remove the solvents and the pore forming agent.

In a preferred embodiment, the porous celecoxib matrix is further processed using standard techniques into tablets or capsules for oral administration or into rectal suppositories, delivered using a dry powder inhaler for pulmonary administration, or mixed/processed into a cream or ointment for topical administration. Alternatively, the porous celecoxib matrix is reconstituted with an aqueous medium and administered parenterally, such as intramuscularly, subcutaneously, or intravenously.

An advantage of the porous drug matrix formulations is that they can be administered as a bolus, when the drug normally must be infused to avoid precipitation of the drug. By avoiding precipitation of drug in vivo, the formulations can also be administered intrarterially, intravenously, locally, intracranially, or intrathecally. An additional advantage is the formulations can be administered in reduced volumes.

In one embodiment, the matrix further includes a pegylated excipient, such as pegylated phospholipid, with the celecoxib. The pegylated excipient shields the drug from macrophage uptake, which prolong its half-life or enhance bioavailability of the drug.

DETAILED DESCRIPTION OF THE INVENTION

Figure 1:
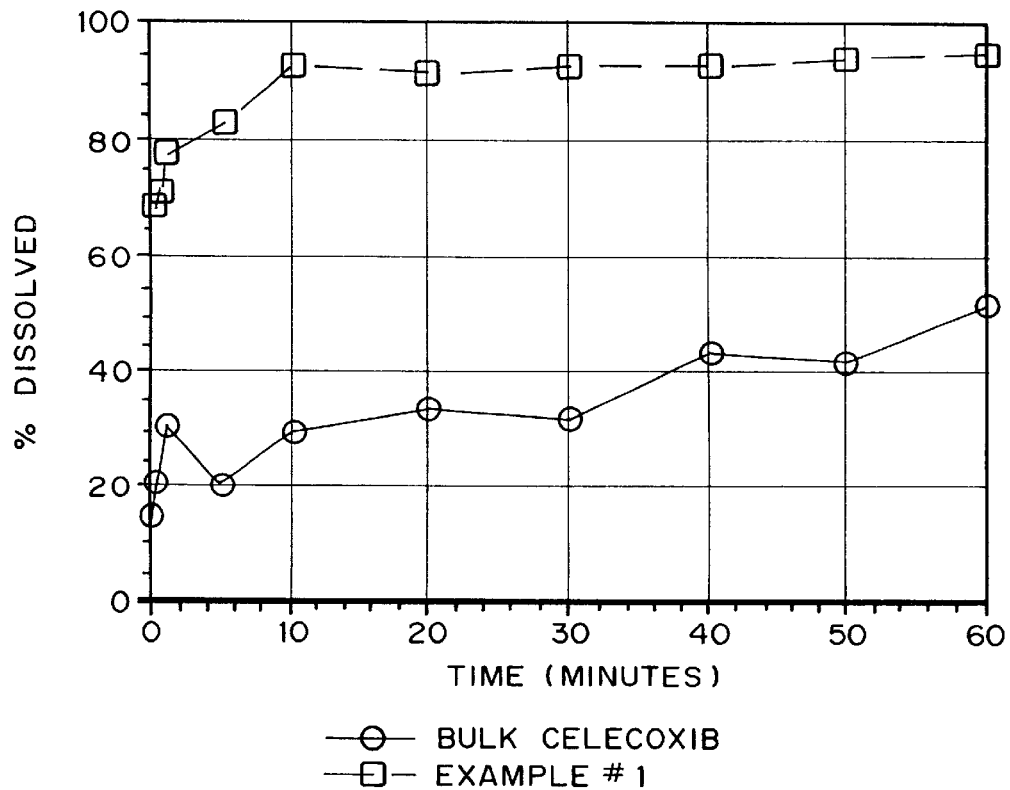
FIG. 1 is a graph of the in vitro dissolution rate (percent dissolved versus time) for non-formulated celecoxib and celecoxib in porous matrix form.

The rate of dissolution of celecoxib can be enhanced by making the drug into a porous matrix form, substantially increasing the surface area of the drug available to contact aqueous biological fluids at the site of administration of the drug composition. The method for making the porous matrix of drug includes the steps of (a) dissolving celecoxib in a volatile solvent to form a drug solution, (b) combining at least one pore forming agent with the drug solution to form an emulsion, suspension, or second solution, and (c) removing the volatile solvent and pore forming agent from the emulsion, suspension, or second solution to yield the porous matrix of celecoxib. In a preferred embodiment, the celecoxib compositions are porous dry powders, which upon the addition of an aqueous medium form a suspension of nanoparticles and microparticles of the drug.

I. Drug Matrix Compositions

The porous drug matrix is at least 1 to 95%, preferably at least about 10%, and more preferably between about 10 and 70%, celecoxib by weight. The matrices also may contain hydrophilic excipients such as water soluble polymers or sugars, wetting agents such as surfactants, and tonicity agents.

The form of the drug matrix (drug powder) is critical to the dissolution rate of the celecoxib. The matrix must contain microparticles of drug, which preferably have a mean diameter between about 0.01 and 5 $\mu$m, more preferably between about 0.1 and 5 $\mu$m. In one embodiment, the mean diameter of the microparticles is between about 0.5 and 5 $\mu$m. The average total surface area of the microparticles contained within the porous matrix, which typically is in the form of a dry powder, is 0.5 $m^2$/mL or greater, preferably 0.9 $m^2$/mL or greater. Total surface area values for the microparticles can be determined using standard Coulter Counter equipment and techniques.

The celecoxib matrix must be sufficiently porous to yield, upon contact with an aqueous medium, microparticles having these parameters. Measurements useful in characterizing the porosity of the drug matrix are the bulk density or the transaxial pressure ("TAP") density of the dry porous matrix (dry powder) and the total surface area (sum of internal and external surface area) of the dry porous matrix. The TAP density preferably is less than or equal to 1.0 g/ml, more preferably less than 0.8 g/ml. This level of porosity of the matrix, characterized by density, provides sufficient surface area to enhance wetting of the dry porous matrix and enhance drug dissolution. The total surface area of the porous matrix can be measured, for example, by BET surface area analysis. In some embodiments, the total surface area of the porous matrix preferably is greater than 0.1 $m^2$/g, more preferably greater than or equal to 0.2 $m^2$/g. This level of total surface area provides sufficient surface area to enhance wetting of the dry porous matrix and enhance drug dissolution.

1. The Drug Celecoxib

Celecoxib is a nonsteroidal anti-inflammatory drug that exhibits anti-inflammatory, analgesic and antipyretic effects. The mechanism of action is believed to be due to inhibition of prostaglandin synthesis, primarily via inhibition of cyclooxygenase-2 (COX-2). The drug is currently used for the treatment of osteoarthritis and rheumatoid arthritis.

As used herein, the term "low aqueous solubility" means that the drug has a solubility of less than about 10 mg/mL, and preferably less than about 5 mg/mL, in aqueous media at approximately physiological temperatures and pH. As used herein, the term "drug" is used interchangeably with "celecoxib" unless otherwise indicated.

2. Excipients

The matrices may contain hydrophilic excipients such as water soluble polymers or sugars which can serve as bulking agents or as wetting agents, wetting agents such as surfactants or sugars, and tonicity agents. Upon contact with an aqueous medium, water penetrates through the highly porous matrix to dissolve the water soluble excipients in the matrix. In the case of low aqueous solubility drugs, a suspension of drug particles in the aqueous medium remains. The total surface area of the resultant low aqueous solubility drug microparticles is increased relative to the unprocessed drug and the dissolution rate of the drug is increased.

One of skill in the art can select appropriate excipients for use in the drug matrix compositions, considering a variety of factors, such as the drug to be administered, the route of administration, the dosage, and the preferred dissolution rate. For example, the excipients can function as bulking agents, release-modifiers, wetting agents, tonicity agents, or combinations thereof. Preferred excipients include hydrophilic polymers, wetting agents, and sugars. The amount of excipient in the drug matrix is less than about 95%, more preferably less than about 80%, by weight of the drug matrix.

The hydrophilic excipients, wetting agents, and tonicity agents may be added to the drug solution, the pore forming agent, or both, during production of the matrix.

(i) Hydrophilic Polymers

The polymers that can be used in the drug matrices described herein include both synthetic and natural polymers, either non-biodegradable or biodegradable. Representative synthetic polymers include polyethylene glycol ("PEG"), polyvinyl pyrrolidone, polymethacrylates, polylysine, poloxamers, polyvinyl alcohol, polyacrylic acid, polyethylene oxide, and polyethyoxazoline. Representative natural polymers include albumin, alginate, gelatin, acacia, chitosan, cellulose dextran, ficoll, starch, hydroxyethyl cellulose, hydroxypropyl cellulose, hydroxy-propylmethyl cellulose, hyaluronic acid, carboxyethyl cellulose, carboxymethyl cellulose, deacetylated chitosan, dextran sulfate, and derivatives thereof. Preferred hydrophilic polymers include PEG, polyvinyl pyrrolidone, poloxamers, hydroxypropyl cellulose, and hydroxyethyl cellulose.

The hydrophilic polymer selected for use in a particular drug matrix formulation is based on a variety of factors, such as the polymer molecular weight, polymer hydrophilicity, and polymer inherent viscosity. The hydrophilic polymer can be used as a bulking agent or as a wetting agent.

(ii) Sugars

Representative sugars that can be used in the drug matrices include mannitol, sorbitol, xylitol, glucitol, ducitol, inositiol, arabinitol, arabitol, galactitol, iditol, allitol, fructose, sorbose, glucose, xylose, trehalose, allose, dextrose, altrose, gulose, idose, galactose, talose, ribose, arabinose, xylose, lyxose, sucrose, maltose, lactose, lactulose, fucose, rhamnose, melezitose, maltotriose, and raffinose. Preferred sugars include mannitol, lactose, sucrose, sorbitol, trehalose, glucose, and are adjusted to provide osmolality if administered parenterally or to provide wetting of the porous drug matrix or the drug microparticles within the matrix.

(iii) Wetting Agents

Wetting agents can be used to facilitate water ingress into the matrix and wetting of the drug particles in order to facilitate dissolution. Representative examples of wetting agents include gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., TWEEN™s), polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxy propylcellulose, hydroxypropylmethylcellulose phthlate, noncrystalline cellulose, magnesium aluminum silicate, triethanolamine, polyvinyl alcohol, and polyvinylpyrrolidone (PVP). Tyloxapol (a nonionic liquid polymer of the alkyl aryl polyether alcohol type, also known as superinone or triton) is another useful wetting agent. Most of these wetting agents are known pharmaceutical excipients and are described in detail in the Handbook of Pharmaceutical Excipients, published jointly by the American Pharmaceutical Association and The Pharmaceutical Society of Great Britain (The Pharmaceutical Press, 1986).

Preferred wetting agents include polyvinylpyrrolidone, polyethylene glycol, tyloxapol, poloxamers such as PLURONIC™ F68, F127, and F108, which are block copolymers of ethylene oxide and propylene oxide, and polyxamines such as TETRONIC™ 908 (also known as POLOXAMINE™ 908), which is a tetrafunctional block copolymer derived from sequential addition of propylene oxide and ethylene oxide to ethylenediamine (available from BASF), dextran, lecithin, dialkylesters of sodium sulfosuccinic acid such as AEROSOL™ OT, which is a dioctyl ester of sodium sulfosuccinic acid (available from American Cyanimid), DUPONOL™ P, which is a sodium lauryl sulfate (available from DuPont), TRITON™ X-200, which is an alkyl aryl polyether sulfonate (available from Rohm and Haas), TWEEN™ 20 and TWEEN™ 80, which are polyoxyethylene sorbitan fatty acid esters (available from ICI Specialty Chemicals), Carbowax 3550 and 934, which are polyethylene glycols (available from Union Carbide), Crodesta F-110, which is a mixture of sucrose stearate and sucrose distearate, and Crodesta SL-40 (both available from Croda Inc.), and SA90HCO, which is $C_{18}H_{37}CH_2(CON(CH_3)CH_2(CHOH)_4CH_2OH)_2$.

Wetting agents which have been found to be particularly useful include Tetronic 908, the Tweens, Pluronic F-68 and polyvinylpyrrolidone. Other useful wetting agents include decanoyl-N-methylglucamide; n-decyl-β-D-glucopyranoside; n-decyl-β-D-maltopyranoside; n-dodecyl-β-D-glucopyranoside; n-dodecyl β-D-maltoside; heptanoyl-N-methylglucamide; n-heptyl-β-D-glucopyranoside; n-heptyl-β-D-thioglucoside; n-hexyl-β-D-glucopyranoside; nonanoyl-N-methylglucamide; n-noyl-β-D-glucopyranoside; octanoyl-N-methylglucamide; n-octyl-β-D-glucopyranoside; and octyl-β-D-thioglucopyranoside. Another preferred wetting agent is p-isononylphenoxypoly (glycidol), also known as Olin-10G or Surfactant 10-G (commercially available as 10G from Olin Chemicals). Two or more wetting agents can be used in combination.

(iv) Tonicity or Osmolality Agents

The porous drug matrices may include one or more tonicity agents, such as salts (e.g., as sodium chloride or potassium chloride) or sugars (such as mannitol, dextrose, sucrose, or trehalose) to adjust a hypotonic solution of a drug to isotonic so that the drug, when in solution, is physiologically compatible with the cells of the body tissue of the patient. The type and amount of tonicity agent can be selected by one of skill in the art using known techniques.

(v) Pegylated Excipients

In one embodiment, the matrix further includes a pegylated excipient. Such pegylated excipients include, but are not limited to, pegylated phospholipids, pegylated proteins, pegylated peptides, pegylated sugars, pegylated polysaccharides, pegylated block copolymers with one of the blocks being PEG, and pegylated hydrophobic compounds such as pegylated cholesterol. The pegylated excipient beneficially envelops or shields the drug from macrophage uptake, which prolongs its half-life or enhances bioavailability of the drug.

Representative examples of pegylated phospholipids include 1,2-diacyl-sn-glycero-3-phosphoethanolamine-N-[Poly(ethylene glycol)2000] ("PEG 2000 PE") and 1,2-diacyl-sn-glycero-3-phosphoethanolamine-N-[Poly (ethylene glycol) 5000] ("PEG 5000 PE"), where the acyl group is selected, for example, from dimyristoyl, dipalmitoyl, distearoyl, dioleoyl, and 1-palmitoyl-2-oleoyl.

Other polyalkyleneoxides can be used in place of the polyethylene.

II. Volatile Solvents

In a preferred embodiment, the solvent is an organic solvent that is volatile, has a relatively low boiling point, or can be removed under vacuum, and which is acceptable for administration to humans in trace amounts. Representative solvents include acetic acid, acetaldehyde dimethyl acetal, acetone, acetonitrile, chloroform, chlorofluorocarbons, dichloromethane, dipropyl ether, diisopropyl ether, N,N-dimethylformamide (DMF), foramide, demethyl sulfoxide (DMSO), dioxane, ethanol, ethyl acetate, ethyl formate, ethyl vinyl ether, methyl ethyl ketone (MEK), glycerol, heptane, hexane, isopropanol, methanol, isopropanol, butanol, triethylamine, nitromethane, octane, pentane, tetrahydrofuran (THF), toluene, 1,1,1-trichloroethane, 1,1,2-trichloroethylene, water, xylene, and combinations thereof. In general, the drug is dissolved in the volatile solvent to form a drug solution having a concentration of between 0.01 and 80% weight to volume (w/v), more preferably between 0.025 and 30% (w/v).

Aqueous solvents or mixtures of aqueous and organic solvents, such as water-alcohol mixtures, can be used to dissolve the celecoxib.

III. Pore Forming Agents

Pore forming agents are volatile materials that are used during the process to create porosity in the resultant matrix. The pore forming agent can be a volatilizable solid or volatilizable liquid.

1. Liquid Pore Forming Agent

The liquid pore forming agent must be immiscible with the drug solvent and volatilizable under processing conditions compatible with the drug. To effect pore formation, the pore forming agent first is emulsified with the drug solvent. Then, the emulsion is further processed to remove the drug solvent and the pore forming agent simultaneously or sequentially using evaporation, vacuum drying, spray drying, fluid bed drying, lyophilization, or a combination of these techniques.

The selection of liquid pore forming agents will depend on the drug solvent. Representative liquid pore forming agents include water; dichloromethane; alcohols such as ethanol, methanol, or isopropanol; acetone; ethyl acetate; ethyl formate; dimethylsulfoxide; acetonitrile; toluene; xylene; dimethylforamide; ethers such as THF, diethyl ether, or dioxane; triethylamine; foramide; acetic acid; methyl ethyl ketone; pyridine; hexane; pentane; furan; water; and cyclohexane.

The liquid pore forming agent is used in an amount that is between 1 and 50% (v/v), preferably between 5 and 25% (v/v), of the drug solvent emulsion.

2. Solid Pore Forming Agent

The solid pore forming agent must be volatilizable under processing conditions which do not harm the drug compositions. The solid pore forming agent can be (i) dissolved in the drug solution, (ii) dissolved in a solvent which is not miscible with the drug solvent to form a solution which is then emulsified with the drug solution, or (iii) added as solid particulates to the drug solution. The solution, emulsion, or suspension of the pore forming agent in the drug solution then is further processed to remove the drug solvent, the pore forming agent, and, if appropriate, the solvent for the pore forming agent simultaneously or sequentially using evaporation, spray drying, fluid bed drying, lyophilization, vacuum drying, or a combination of these techniques.

In a preferred embodiment, the solid pore forming agent is a volatile salt, such as salts of volatile bases combined with volatile acids. Volatile salts are materials that can transform from a solid or liquid to a gaseous state using added heat and/or vacuum. Examples of volatile bases include ammonia, methylamine, ethylamine, dimethylamine, diethylamine, methylethylamine, trimethylamine, triethylamine, and pyridine. Examples of volatile acids include carbonic acid, hydrochloric acid, hydrobromic acid, hydroiodic acid, formic acid, acetic acid, propionic acid, butyric acid, and benzoic acid. Preferred volatile salts include ammonium bicarbonate, ammonium acetate, ammonium chloride, ammonium benzoate and mixtures thereof.

Other examples of solid pore forming agents include iodine, phenol, benzoic acid (as acid not as salt), and naphthalene.

The solid pore forming agent is used in an amount between 0.5 and 1000% (w/w), preferably between 10 and 600% (w/w), and more preferably between 1 and 100% (w/w), of the drug.

IV. Method of Making the Porous Drug Matrix

The porous drug matrices preferably are made by (i) dissolving the celecoxib in a volatile solvent to form a drug solution, (ii) combining at least one pore forming agent with the drug solution to form an emulsion, suspension, or second solution, and (iii) removing the volatile solvent and pore forming agent from the emulsion, suspension, or second solution. In a preferred embodiment, spray drying, optionally followed by lyophilization or vacuum drying, is used to remove the solvents and the pore forming agent. The removal of the pore forming agent can be conducted simultaneously with or following removal of enough solvent to solidify the droplets. Production can be carried out using continuous, batch, or semi-continuous processes.

First, the celecoxib is dissolved in an appropriate solvent. The concentration of the drug in the resulting drug solution typically is between about 0.01 and 80% (w/v), preferably between about 0.025 and 30% (w/v).

Next, the drug solution is combined, typically under mixing conditions, with the pore forming agent or solution thereof. If a liquid pore forming agent is used, it is first emulsified with the drug solution to form droplets of pore forming agent dispersed throughout the drug solution. If a solid pore forming agent is used, it is dissolved either directly in the drug solution to form a solution of drug/pore forming agent, or it is first dissolved in a second solvent. If the second solvent is immiscible with the drug solvent, the solution of the pore forming agent is emulsified with the drug solution to form droplets of the pore forming agent solution dispersed throughout the drug solution. If the second solvent is miscible with the drug solution, the two solutions are mixed to form a single drug solution. A solid pore forming agent alternatively can be added directly to the drug solution as solid particulates, preferably between about 100 nm and 10 $\mu$m in size, to form a suspension of pore forming agent in the drug solution. Subsequently, the solid pore forming agent particle size can be reduced by further processing the resulting suspension, for example, using homogenization or sonication techniques known in the art.

Then, the solution, emulsion, or suspension is further processed to remove the drug solvent and the pore forming agent simultaneously or sequentially, using evaporation, spray drying, fluid bed drying, lyophilization, vacuum drying, or a combination of these techniques. In a preferred embodiment, the solution, emulsion, or suspension is spray-dried. As used herein, "spray dry" means to atomize the solution, emulsion, or suspension to form a fine mist of droplets (of drug solution having solid or liquid pore forming agent dispersed throughout), which immediately enter a drying chamber (e.g., a vessel, tank, tubing, or coil) where they contact a drying gas. The solvent and pore forming agents evaporate from the droplets into the drying gas to solidify the droplets, simultaneously forming pores throughout the solid. The solid (typically in a powder, particulate form) then is separated from the drying gas and collected.

The temperature of the inlet and outlet ports of the drying chamber, as well as the flow rates of the feed solution, atomization gas, and drying gas, can be controlled to produce the desired products. In a particularly preferred embodiment, the spray drying methods described in U.S. Pat. No. 5,853,698 to Straub et al. are adapted to make the drug matrices.

The drug present in the solids or powder produced may be in a crystalline or an amorphous state, or may be mixture of such states. The state generally depends on how the droplets are dried and the excipients present.

Emulsion Stabilization

In embodiments in which at least one pore forming agent is combined with the drug solution to form an emulsion, a surfactant or emulsifying agent can be added to enhance the stability of the emulsion. A variety of surfactants may be incorporated in this process, preferably to an amount between 0.1 and 5% by weight. Exemplary emulsifiers or surfactants which may be used include most physiologically acceptable emulsifiers, for instance egg lecithin or soya bean lecithin, or synthetic lecithins such as saturated synthetic lecithins, for example, dimyristoyl phosphatidyl choline, dipalmitoyl phosphatidyl choline or distearoyl phosphatidyl choline or unsaturated synthetic lecithins, such as dioleyl phosphatidyl choline or dilinoleyl phosphatidyl choline. Other hydrophobic or amphipathic compounds can be used in place of the phospholipid, for example, cholesterol. Emulsifiers also include surfactants such as free fatty acids, esters of fatty acids with polyoxyalkylene compounds like polyoxpropylene glycol and polyoxyethylene glycol; ethers of fatty alcohols with polyoxyalkylene glycols; esters of fatty acids with polyoxyalkylated sorbitan; soaps; glycerol-polyalkylene stearate; glycerol-polyoxyethylene ricinoleate; homo- and co-polymers of polyalkylene glycols; polyethoxylated soya-oil and castor oil as well as hydrogenated derivatives; ethers and esters of sucrose or other carbohydrates with fatty acids, fatty alcohols, these being optionally polyoxyalkylated; mono-, di- and tri-glycerides of saturated or unsaturated fatty acids, glycerides of soya-oil and sucrose.

Other emulsifiers include natural and synthetic forms of bile salts or bile acids, both conjugated with amino acids and unconjugated such as taurodeoxycholate and cholic acid.

V. Porous Drug Matrix Applications

The porous celecoxib matrices described herein are useful in formulations for administration to a patient in need of the drug. As used herein, "patient" refers to animals, including mammals, preferably humans. The formulations deliver a therapeutically or prophylactically effective amount of the drug to the patient.

The celecoxib formulations described herein are useful, for example, as anti-inflammatory, analgesic, and antipyretic therapeutic agents. The drug is currently used for the treatment of osteoarthritis and rheumatoid arthritis. Other treatments using celecoxib are described, for example, in U.S. Pat. No. 6,046,191, which is incorporated by reference.

The porous matrices, or formulations thereof, are suitable for administration of celecoxib by a variety of routes, for example, parenteral, mucosal, oral, topical/transdermal administration, for local, regional, or systemic effect. Examples of parenteral routes include intraveneous, intraarterial, intracardiac, intrathecal, intraosseous, intraarticular, intrasynovial, intracutaneous, subcutaneous, and intramuscular administration. Examples of mucosal routes include pulmonary (intrarespiratory), buccal, sublingual, intranasal, rectal, and vaginal administration. The porous matrices also can be formulated for intraocular, conjunctival, aural, urethral, intracranial, intralesional, and intratumoral administration.

In a preferred embodiment, the celecoxib matrix is in the form of powder, which can be reconstituted with an aqueous medium, such as physiological saline, and administered parenterally, such as intramuscularly, subcutaneously, or intravenously. An advantage of the formulations described herein is that they can be used to convert drugs which must be infused (e.g., to avoid precipitation of the drug following bolus injection) to a bolus formulation, avoiding unacceptable precipitation of drug in vivo or for local delivery.

Alternatively, the matrix can be further processed using standard techniques into tablets or capsules for oral administration, into rectal suppositories, into a dry powder inhaler for pulmonary administration, or mixed/processed into a cream or ointment for topical administration. These standard techniques are described, for example, in Ansel, et al., "Pharmaceutical Dosage Forms and Drug Delivery Systems," $6^{th}$ Ed., (Williams & Wilkins 1995).

The present invention will be further understood with reference to the following non-limiting examples.

Materials and Equipment Used in the Examples

The following materials were obtained from Spectrum Chemicals, Gardena, Calif.: sodium dodecyl sulfate (SDS), mannitol, ammonium bicarbonate, polyvinylpyrrolidone K-30, and ethanol. Celecoxib was obtained from Cipla Ltd, Mumbai, India. Solutions were mixed using a magnetic stirbar and a digital hotplate/stirrer (model 04644, Cole Parmer, Vernon Hills, Ill.). All solutions were spray dried on a benchtop spray dryer using an air-atomizing nozzle. The overhead mixer used for the dissolution studies was an IKA RW16 Basic Mixer with a R1342 propeller shaft.

EXAMPLE 1

Production of a Porous Celecoxib Matrix

A celecoxib-loaded organic solution was prepared by dissolving 1.0 g of celecoxib and 0.10 g of polyvinylpyrrolidone K-30 in 160 ml of ethanol. An aqueous solution composed of 0.42 g of ammonium bicarbonate, 1.0 g of mannitol, and 0.10 g of sodium dodecyl sulfate (SDS) in 40 ml of DI water was added to the ethanol solution and mixed. The resulting 80% ethanol solution was spray dried using nitrogen as both the atomizing and drying gas. Spray drying conditions were as follows: 30 ml/min solution flow rate, 30 L/min atomization gas rate, 100 kg/hr drying gas rate, and 30° C. outlet temperature.

EXAMPLE 2

In vitro Dissolution of a Porous Celecoxib Matrix

Dissolution studies for celecoxib were conducted in phosphate buffered saline containing 0.08% Tween 80 (T80/PBS) at room temperature in a glass beaker using overhead mixing with the stirring rate set to 5. T80/PBS (700 mL) was added to an appropriate amount of material being tested to contain 2.45 mg of celecoxib. Samples were removed via pipet and filtered through 0.22 $\mu$m CA syringe filter. Samples were analyzed via UV-vis spectroscopy (Hewlett Packard Model 8453) for celecoxib using 249 nm. As shown in FIG. 1, the celecoxib from the supplier was 50% dissolved after 1 hour, while the porous celecoxib matrix produced in Example 1, in contrast, was essentially fully dissolved after 10 minutes. The data in FIG. 1 is shown as percent of complete dissolution.

Modifications and variations of the present invention will be obvious to those of skill in the art from the foregoing detailed description. Such modifications and variations are intended to come within the scope of the following claims.

We claim:

1. A method for making a porous matrix of celecoxib comprising
   (a) dissolving celecoxib in a volatile solvent to form a drug solution,
   (b) combining at least one pore forming agent with the drug solution to form an emulsion, suspension, or second solution, and
   (c) removing the volatile solvent and pore forming agent from the emulsion, suspension, or second solution to yield the porous matrix of celecoxib,
      wherein upon exposure to an aqueous medium, the matrix dissolves to leave nanoparticles and microparticles of celecoxib.

2. The method of claim 1 further comprising incorporating at least one wetting agent into the emulsion, suspension, or second solution.

3. The method of claim 1 wherein step (c) is conducted using a process selected from spray drying, evaporation, fluid bed drying, lyophilization, vacuum drying, or a combination thereof.

4. The method of claim 1 wherein the drug solution or pore forming agent further comprises an excipient selected from the group consisting of hydrophilic polymers, sugars, pegylated excipients, and tonicity agents.

5. The method of claim 1 wherein the pore forming agent is a volatile salt.

6. The method of claim 5 wherein the volatile salt is selected from the group consisting of ammonium bicarbonate, ammonium acetate, ammonium chloride, ammonium benzoate, and mixtures thereof.

7. The method of claim 1 which yields a porous matrix formed of a wetting agent and microparticles of a drug, wherein the microparticles have a mean diameter between about 0.01 and 5 μm and a total surface area greater than about 0.5 m²/mL, and wherein the porous matrix is in a dry powder form.

8. A pharmaceutical composition comprising a porous matrix which comprises a wetting agent and nanoparticles and microparticles of celecoxib,
   wherein the nanoparticles and microparticles have a mean diameter between about 0.01 and 5 μm and a total surface area greater than about 0.5 m²/mL, and
   wherein the porous matrix has a TAP density less than or equal to 1.0 g/mL and/or has a total surface area of greater than or equal to 0.2 m²/g and is in the form of a dry powder, and
   wherein upon exposure to an aqueous medium, the matrix dissolves to leave the nanoparticles and microparticles of celecoxib.

9. The composition of claim 8 wherein the dry powder form of the porous matrix has a TAP density less than or equal to 1.0 g/mL.

10. The composition of claim 9 wherein the matrix upon contact with an aqueous medium yields microparticles having a mean diameter between about 0.1 and 5 μm and a total surface area greater than about 0.5 m²/mL.

11. The composition of claim 8 wherein the matrix further comprise an excipient selected from the group consisting of hydrophilic polymers, sugars, tonicity agents, pegylated excipients, and combinations thereof.

12. The composition of claim 8 wherein the mean diameter of the microparticles is between about 0.01 and 5 μm.

13. The composition of claim 12 wherein the mean diameter of the microparticles is between about 0.5 and 5 μm.

14. The composition of claim 13 wherein the mean diameter of the microparticles is between about 1 and 5 μm.

15. The composition of claim 8 wherein the microparticles are suspended in an aqueous solution suitable for parenteral administration.

16. The composition of claim 8 wherein the matrix is processed into tablets or capsules suitable for oral administration.

17. The composition of claim 8 wherein the matrix is formed into suppositories suitable for vaginal or rectal administration.

18. The composition of claim 8 wherein the matrix is in a dry powder form suitable for pulmonary administration.

19. The composition of claim 8 wherein the porous matrix is made by a process comprising
   (a) dissolving celecoxib in a volatile solvent to form a drug solution,
   (b) combining at least one pore forming agent with the drug solution to form an emulsion, suspension, or second solution,
   (c) incorporating at least one wetting agent into the emulsion, suspension, or second solution, and
   (d) removing the volatile solvent and pore forming agent from the emulsion, suspension, or second solution to yield the porous matrix.

20. A method of delivering celecoxib to a patient in need thereof, comprising
   administering a therapeutically or prophylactically effective amount of celecoxib in a formulation comprising the composition of claim 8.

21. The method of claim 20 wherein the formulation is suitable for administration by a route selected from the group consisting of parenteral, mucosal, oral, and topical administration.

22. The method of claim 21 wherein the parenteral route is selected from the group consisting of intraveneous, intraarterial, intracardiac, intrathecal, intraosseous, intraarticular, intrasynovial, intracutaneous, subcutaneous, and intramuscular administration.

23. The method of claim 21 wherein the mucosal route is selected from the group consisting of pulmonary, buccal, sublingual, intranasal, rectal, and vaginal administration.

24. The method of claim 21 wherein the formulation is suitable for intraocular or conjunctival administration.

25. The method of claim 21 wherein the formulation is in an aqueous solution suitable for parenteral administration.

* * * * *